United States Patent [19]

Schulz et al.

[11] 3,980,791

[45] Sept. 14, 1976

[54] TETRAMISOLE AND LEVAMISOLE POUR-ON ANTHELMINTIC COMPOSITIONS AND METHODS OF USE

[75] Inventors: Hans Peter Schulz, Wuppertal; Herbert Voege, Opladen-Bruchhausen, both of Germany

[73] Assignee: Bayer Aktiengesellschaft, Germany

[22] Filed: Dec. 13, 1974

[21] Appl. No.: 532,595

Related U.S. Application Data

[63] Continuation-in-part of Ser. No. 480,110, June 17, 1974, abandoned.

[30] Foreign Application Priority Data

June 22, 1973 Germany............................ 2331793

[52] U.S. Cl................................ 424/270; 424/358
[51] Int. Cl.²..................................... A61K 31/425
[58] Field of Search............................ 424/270, 358

[56] References Cited
UNITED STATES PATENTS 3,642,809  2/1972  Bullock................................ 424/270

OTHER PUBLICATIONS

Herlich et al, "Anthel. Activity of Ruelene Ad. to Cattle Orally & Topically", Vet. Med., May, 1961 (pp. 219–221).

Hotson, "Anthelmintics for Cattle" Aust. Vet. Journal, vol. 39 (1963) pp. 108–115.

Poole et al, "Anthel. Efficacy of Topically Applied Ctufomate Against Gastrointestinal Parasites in Cattle," Am. J. Vet. Res. 33 (1972), p. 1063–1066.

Lyons et al, Am. J. Vet. Res., vol. 33, No. 1 (1972), pp. 65–70.

Merck Index, 7th Cd. (1960), pp. 579, 788, 833.

Primary Examiner—V. D. Turner

[57] ABSTRACT

Pour-on veterinary compositions are prepared which comprise an anthelmintically effective amount of tetramisole, levamisole or an acid addition salt thereof in combination with a diluent suitable for pour-on formulations for use on animals. These compositions are used to treat helminthic infestations in animals by the pour-on method of application.

47 Claims, No Drawings

TETRAMISOLE AND LEVAMISOLE POUR-ON ANTHELMINTIC COMPOSITIONS AND METHODS OF USE

This is a continuation-in-part of application Ser. No. 480,110 filed June 17, 1974, now abandoned.

The present invention is concerned with pour-on veterinary compositions and methods of treating helminthic infestations in animals by the pour-on-application method wherein the active agent in said pour-on compositions is tetramisole, levamisole or an acid addition salt thereof.

By "pour-on" veterinary composition is meant a composition that is applied directly to the external skin of the animal. This may be effected by pouring the composition on or over the animal's external skin, by spraying the composition on all or a portion of the animal's external skin (as, for example, from a measuring vessel, a spray flask, an aerosol pack, or the like), or by drenching or otherwise immersing all or a part of the animal's external skin in the composition.

The "pour-on" method of application is known. For example, phosphoric acid esters such as Ruelene (i.e., 4-tertiary-butyl-2-chlorophenyl N-methyl-O-methyl-phosphonamidate), Trichlorphon (i.e., dimethyl-[2,2,2-trichloro-1-hydroxyethyl]-phosphonate), Fenthion (i.e. O,O-dimethyl-O-(4-methylmercapto-3-methylphenyl)-thionophosphate) and others, which in addition to an anthelmintic action also possess a very pronounced insecticidal action, are administered by pouring on. However, the anthelmintic action of Trichlorphon and Fenthion via pour-on administration is only slight, and distinctly less than that which is achieved via oral or subcutaneous administration. In the case of Fenthion it was also found that the action against lung worm (Dictyocaulus) was only detectable in some of the cattle treated by pour-on application.

The pour-on administration of Ruelene for use against infection with endoparasitic worms has also been attempted but the anthelmintic action thereby achieved is generally insufficient for practical purposes.

As a rule, the anthelmintic action of a given preparation is substantially more pronounced when the preparation is orally or parenterally administered than when it is administered by pouring-on (Herlich et al., Veterinary Medicine 56, 219–221 (1961); Hotson, Australian Vet. J. 39, 108–115 (1963)).

However, the pour-on application of a suitable composition can offer distinct advantages in comparison to oral or parenteral administration, particularly in veterinary practice. For example, the animals to be treated need not be held and, therefore, there is less danger of injury to the animals and to persons carrying out the treatment. This method of application has particular value in the treatment of neats since these animals do not lend themselves to oral or parenteral application. In addition, there is substantially less danger of transmission of infectious diseases, and there are substantially slighter local non-toleration symptoms and less apparatus is required than in the case of administration by injection.

There is, therefore, a genuine need for a method of combatting helminthic infestation which uses the "pour-on" method of administration. We have now discovered that this can be achieved while still affording an anthelmintic effect which is comparable to that obtained by oral or parenteral administration.

It is surprising that the pour-on veterinary compositions of the presention wherein the active ingredient is tetramisole, levamisole, or an acid addition salt thereof, exhibit good anthelmintic activity according to the pour-on application because other known antihelmintics such as Ruelene and Trichlorphon exhibit a much stronger level of activity on oral and parenteral administration than they do when utilized in pour-on administration.

The present method, therefore, represents an advance in veterinary medicine and has the distinct advantage of being simple and reliable. In contrast to injection or parenteral administration the animals need not be held. In general, it is sufficient if the animals, e.g. cattle, sheep or pigs, are herded into sheds, runs or a fenced-off grazing area or driven through a passage where the preparation is administered. The animals need not be tied up or held, as in the case of oral or parenteral administration.

It is obvious that such simple handling minimizes the danger of injury to persons who carry out the administration. Likewise, there is no danger of injury to the animals as can be the case when a needle is wrongly inserted as, for example, when the needle is inserted intramuscularly instead of subcutaneously or into the vicinity of a nerve, fasciae or bone. Even oral administration can result in injury to the animal as in the case of intratracheal administration or by injury to the palate.

An additional advantage to pour-on administration is that during treatment campaigns the danger of transmission of infectious diseases, for example, swine plague, foot-and-mouth disease, bovine leucosis, symptomatic anthrax, swine erysipelas, brucellosis, infectious anaemia of horses, is substantially eliminated.

The pour-on method of administration also eliminates the danger of forcing particles of dirt and germs under the skin during injection, which can occur when performed at inadequately disinfected parts of the skin and their sequelae. Also, in comparison to subcutaneous or intramuscular injection there is very little danger with pour-on administration of local intolerance caused by depositing a large quantity of preparation on a very limited area of tissue. In contrast to administration by injection, pouring and spraying on of the solution causes the animals no pain and does not provoke them into making defensive movements. As with injections or oral administration, the individual animal can be given an exact dose of the preparation when using pour-on administration. This ensures that each treated animal receives an economic but reliably effective dosage in contrast to administration via the fodder or drinking water.

Pour-on administration also has the advantage of requiring little apparatus. Sharp needles for injection or drench devices for oral treatment can be dispensed with and can be replaced, for example, by a measuring device which is emptied over the back of the animal or by devices with which the measured amount of preparation can be sprayed onto the animal.

The pour-on veterinary compositions of the present invention are prepared by dissolving, emulsifying or suspending tetramisole, levamisole, or an acid addition salt thereof, in a diluent suitable for pour-on application to animals. The compositions may, if desired, contain other pharmaceutically active compounds such as other anthelmintics.

The compositions of the present invention may be in any liquid form which is suitable for pour-on administration. In particular said compositions may be in the form of a solution as, for example, where the active ingredient is dissolved in a suitable diluent, or it may be in the form of a suspension or emulsion as, for example, where the active ingredient is suspended or emulsified in a suitable diluent.

The term "diluent" refers to a nontoxic pharmacologically acceptable carrier which, when mixed with the active ingredient, renders it suitable for pour-on administration. The diluent must be sufficiently compatible with the active ingredient as to permit adequate concentrations of the latter. In addition, the diluent must not inhibit adequate resorption of the active ingredient through the skin and, also, it must be sufficiently nontoxic as to avoid damaging the animal tissues with which it comes in contact. Typical of the diluents which may be employed are for example: water, mono- and polyhydric alcohols (e.g. ethanol, isopropanol, benzyl alcohol, propylene glycol, 1,3-butylene glycol, glycerol, tetrahydrofurfuryl alcohol, and polyethylene glycol), liquid esters (e.g. ethyl carbonate, ethyl acetate, isopropyl myristate, benzyl benzoate, caprylic and caproic acid triglycerides and ethyl lactate), natural oils (e.g. cottonseed, groundnut, maize germ, olive, castor and sesame oils), waxy fatty acid esters (e.g. duck uropygeal gland fat), aliphatic and aromatic hydrocarbons (e.g. decahydronaphthalene), ketones such as lower alkyl ketones, lower cycloalkanones and N-lower alkyl pyrrolidones (e.g., acetone, methyl ethyl ketone, cyclohexanone and N-methyl-pyrrolidone), ethers (e.g., dioxane), amides (e.g., dimethylformamide), dimethylsulphoxide, and 2-dimethyl-4-hydroxymethyl-1,3-dioxalane. Particularly suitable diluents include the alcohols, for example, the lower alkanols such as ethanol and isopropanol, the glycols, for example, the lower alkylene glycols such as ethylene glycol, propylene glycol and butylene glycol, the lower cycloalkanones such as cyclohexanone and tetrafurfuryl alcohol.

The compositions used in this invention may also contain conventional adjuvants and modifiers such as adhesion promoters and surface-active agents. Typical of these are the following:

a. adhesion promoters such as cellulose derivatives (e.g. carboxymethyl cellulose and methylcellulose), starch derivatives, polyacrylates, alginates, gelatine, gum arabic, polyvinylpyrrolidone, polyvinyl alcohol, methyl vinyl ether and maleic anhydride copolymers, and polyethylene glycols; and b. surface-active agents, including emulsifiers and wetting agents and, frequently, substances which assist resorption as, for example:
   1. anionic surface-active agents (e.g. sodium lauryl sulphate, fatty alcohol ether sulphates and monoor dialkylpolyglycol ether orthophosphoric acid ester monoethanolamine salt);
   2. cationic surface-active agents (e.g. cetyltrimethylammonium chloride);
   3. ampholytic surface-active agents (e.g. disodium-N-lauryl-β-iminodipropionate and lecithin); and
   4. nonionic surface-active agents (e.g. polyoxyethylated castor oil, polyoxyethylated sorbitane monooleate, sorbitane monostearate, ethyl alcohol, glycerine monostearate, polyoxyethylene stearate and alkylphenol polyglycol ethers).

When the composition is intended for spraying as an aerosol it will generally contain one of the adhesion promoters mentioned under (a), supra, as well as one of the emulsifiers mentioned under (b), supra. Compositions for spraying can additionally contain the customary propellants as, for example, a chlorofluorohydrocarbon and/or butane.

Compositions used according to the invention which are suspensions may contain a surface-active agent as, for example, one or more of the surface-active agents indicated under item (b) above, a polyoxyethylene sorbitane ester, a glycerine monostearate and a thickener such as one or more of those recited above such as colloidal silica, methylcellulose, aluminium monostearate, polyacrylic acid derivatives and microcrystalline cellulose.

The compositions of the present invention may be made up before use in unit dosage form. This means that the composition is made up into physically discrete coherent portions suitable for pour-on administration and that each portion contains a daily dose of the active ingredient or a multiple thereof of up to about four times the daily dose. Alternatively, the composition may be made up into a physically discrete portion containing a submultiple of a daily dose, down to about a fortieth of the daily dose. Whether the unit dosage form contains a daily dose or a half, a third or a quarter of said daily dosage will depend upon whether the composition is to be administered once, twice, three times or four times a day respectively. Typical examples of unit dosage forms are sealed vials each containing a daily dose of the composition and which may be opened immediately before use and poured onto the animal's back. By this procedure, one can avoid having to measure out each dose of the composition to be administered at the situs and immediately before administration.

The compositions of the present invention should contain from about 1.0 to 20.0 percent by weight of active ingredient, and, preferably, from about 5.0 to 15.0 percent by weight of active ingredient.

In general, it has proved advantageous to apply amounts of from about 1 mg to about 20 mg of the active ingredient per kg of body weight per day of the animal being treated in order to achieve effective results.

For the animals of which the treatment is of principal interest, the following dosage rates have proved to be suitable.

| Animal | mg of active ingredient per kg of body weight |
|---|---|
| sheep | 5 – 10 |
| neats | 5 – 15 |
| dogs | 8 – 12 |
| pigs | 10 – 20 |

According to one embodiment of the present invention, a pour-on veterinary composition is produced which comprises 1 to 20 percent, especially 5 to 15 percent, by weight of tetramisole, levamisole, or an acid addition salt thereof, in combination with from 10 to 94 percent, especially from 60 to 90 percent, of an aliphatic alcohol preferably of 2 to 8 carbon atoms, and especially alkanol of 2 to 8 carbon atoms, and from 5 to 89 percent, especially 5 to 30 percent, by weight of a liquid paraffin, especially a light and purified spindle oil distillate. Alkanols of 2 to 4 carbon atoms have been found to be useful, especially because of their ready availability. Representative formulations include: 10 g levamisol, 63.3 g isopropanol, and 10 g viscous paraffin; and 10 percent levamisole, 80 percent isopropanol and 10 percent light and purified spindle oil distillate.

According to another embodiment of the present invention, a pour-on veterinary composition is produced which comprises 1 to 20 percent, especially 5 to 15 percent, by weight of tetramisole, levamisole, or an acid addition salt thereof, in combination with 10 to 94 percent, especially 60 to 90 percent, by weight of an ester of an aromatic acid, especially esters of phthalic acid, particularly the mono- and di-lower alkyl esters, such as for example, an ester of phthalic acid and from 5 to 50 percent by weight of a nonionic surface active agent, especially esters of sorbitan and fatty acids with and without polyoxyethylene.

The following examples illustrate the method by which the above-described compositions may be employed. In the said examples, the terms "Tetramisole", "Levamisole" and "LPS" have the following definitions:

"Tetramisole" means D,L-(2,3,5,6)-tetrahydro-6-phenyl-imidazo-(2,1-b)thiazole.

"Levamisole" means L-(2,3,5,6)-tetrahydro-6-phenyl-imidazo-(2,1-b)thiazole.

"LPS" means light and purified spindle oil distillate.

Tables I–VIII in Examples A, B and C which follow indicate the anthelmintic compound employed in the following studies, the diluent used, the mode of application and the minimum dosage designated in mg of active ingredient/kg of body weight which effected more than 90 percent of the worms to be expelled.

EXAMPLE A

Strongyloides ratti/rats

Test animals infected with *Strongyloides ratti* were treated at the end of the prepatency period of the parasites. A solution of the active compound was applied by pouring-on.

The activity of the composition was determined by counting, after dissection of the animals, the worms remaining in the test animal, comparing the result with that obtained for untreated control animals and calculating the percentage action.

The results of this study are given in Table I and II below:

TABLE I

| Solvent | Active ingredient: Tetramisole | |
|---|---|---|
| | Type of application | Effective minimum dose |
| Isopropanol | pour-on | 25 |
| H₂O | subcutaneous | 25 |
| Isopropanol + LPS (10%) | pour-on | 10 |
| Known preparation for comparison - Active ingredient: Trichlorphon | | |
| Isopropanol | pour-on | inactive at 250 mg/kg |
| Isopropanol + LPS (10%) | pour-on | inactive at 250 mg/kg |

TABLE II

| Solvent | Active ingredient: Tetramisole HCL | |
|---|---|---|
| | Type of application | Effective minimum dose |
| Polyethylene glycol 200 | pour-on | 10 |
| Ethylene glycol | pour-on | 10 |
| Cyclohexanone | pour-on | 25 |
| Tetrahydrofurfuryl alcohol | pour-on | 100 |
| Isopropanol | pour-on | 10 |
| H₂O | subcutaneous | 25 |
| Isopropanol + LPS (10%) | pour-on | 10 |
| Known preparation for comparison - Active ingredient: Trichlorphon | | |
| Polyethylene glycol 200 | pour-on | inactive at 250 mg/kg |
| Ethylene glycol | pour-on | inactive at 250 mg/kg |
| Tetrahydrofurfuryl alcohol | pour-on | inactive at 250 mg/kg |

EXAMPLE B

Nippostrongylus muris/rats

Test animals infected with *Nippostrongylus muris* are treated at the end of the prepatency period of the parasites. A solution of the active compound was applied by pouring-on.

The activity of the formulation is determined by counting, after dissection of the animal, the worms remaining in the test animal, comparing the result to that obtained with untreated control animals, and calculating the percentage action.

The results of this study are indicated in Tables III and IV below:

TABLE III

| Solvent | Active ingredient: Tetramisole | |
|---|---|---|
| | Type of application | Effective minimum dose |
| Butylene glycol | pour-on | inactive |
| Propylene glycol | pour-on | inactive |
| Isopropanol | pour-on | 50 |
| H₂O | subcutaneous | 25 |
| Isopropanol + LPS (10%) | pour-on | 50 |
| Known preparation for comparison - Active ingredient: Trichlorphon | | |
| Isopropanol | pour-on | inactive at 250 mg/kg |

TABLE IV

| Solvent | Active ingredient: Tetramisole, Hydrochloride | |
|---|---|---|
| | Type of application | Effective minimum dose |
| Polyethylene glycol 200 | pour-on | 50 |
| Ethylene glycol | pour-on | 50 |
| Cyclohexanone | pour-on | 25 |
| Isopropanol | pour-on | 25 |
| H₂O | subcutaneous | 25 |
| Known preparation for comparison - Active ingredient: Trichlorphon | | |

TABLE IV-continued

| | | |
|---|---|---|
| Polyethylene glycol 200 | pour-on | inactive at 250 mg/kg |
| Ethylene glycol | pour-on | inactive at 250 mg/kg |
| Tetrahydrofurfuryl alcohol | pour-on | inactive at 250 mg/kg |

EXAMPLE C

Ascaris suum larvae/rats

Test animals infected with *Ascaris suum* are treated 1–3 days are infection. A solution of the active compound was applied by pour-on administration.

The activity of the formulation is determined by dissection on the 7th day after infection, counting the worms remaining in the test animal, comparing the result to that obtained for untreated control animals, and calculating the percentage action.

The results of this study are indicated in Tables V–VI below:

TABLE V

| | Active ingredient: Tetramisole | |
|---|---|---|
| Solvent | Type of application | Effective minimum dose |
| Isopropanol | pour-on | 25 |
| Isopropanol + 10% LPS | pour-on | 25 |
| Known preparation for comparison- | | |
| | Active ingredient: Trichlorphon | |
| Isopropanol | pour-on | inactive at 250 mg/kg |
| Isopropanol + 10% LPS | pour-on | inactive at 250 mg/kg |

TABLE VI

| | Active ingredient: Tetramisole, Hydrochloride | |
|---|---|---|
| Solvent | Type of application | Effective minimum dose |
| Polyethylene glycol 200 | pour-on | 50 |
| Ethylene glycol | pour-on | 50 |
| Cyclohexanone | pour-on | 50 |
| Isopropanol | pour-on | 50 |

The values given in the following tables VII and VIII relate to the local tolerance of some solvents used in rat tests and not to the biological effectiveness of said compositions.

TABLE VII

| | Active ingredient: Tetramisole | | | |
|---|---|---|---|---|
| | Penetrating capacity/skin tolerance - Test animal: rat | | | |
| Solvent | Application | Wetting | Penetrating capacity | Skin tolerance |
| Butylene glycol | pour-on | good | immediate | no symptoms* |
| Propylene glycol | pour-on | good | after 3–5 mins. | no symptoms |
| Isopropanol | pour-on | good | after 1–2 mins. | no symptoms |

*no local non-tolerance

EXAMPLE D

Lung worm test in bovine cattle

Neats infected experimentally or naturally with Dictyocaulus are treated by pouring the solution of active compound onto their backs or by subcutaneous injection.

The activity is determined by quantitatively counting the lung worm larvae expelled in the faeces before and after the treatment.

A decrease in the larvae expelled after the treatment indicates that the worms have been killed or damaged so muct that they cannot produce any more larvae.

The results of this study are indicated in Table IX below:

TABLE IX

| Preparation/application | Dose (mg/kg) | Larvae Reduction (%) |
|---|---|---|
| 10% by weight of Levamisole in isopropanol + 10% by weight of LPS pour-on | 10 | 100 |
| | 7.5 | 99 |
| | 5 | 99 |
| 10% strength aqueous Levamisole solution*, subcutaneous | 5 | 98 |

*Known preparation for comparison

EXAMPLE E

Gastro-intestinal worm test/controlled test against adults

Neats experimentally infected with Haemonchus, Cooperia and Oesophagostomum were treated by pouring the solution of active compound onto their backs.

The activity of the preparation is determined by dissecting the animal, counting the worms remaining, comparing the result with that of untreated control animals, and calculating the percentage action.

The results of this study are indicated in Table X below:

TABLE VIII

| | Active ingredient: Tetramisole, Hydrochloride | | | |
|---|---|---|---|---|
| | Penetrating capacity/skin tolerance - Test animal: rat | | | |
| Solvent | Application | Wetting | Penetrating capacity | Skin tolerance |
| Polyethylene glycol 200 | pour-on | poor | after about 15 mins. | no symptoms |
| Ethylene glycol | pour-on | good | after about 10–15 mins. | no symptoms |
| Cyclohexanone | pour-on | good | after about 10–15 mins. | no symptoms |
| Tetrahydrofurfuryl alcohol | pour-on | poor | after about 15 mins. | no symptoms |
| Isopropanol | pour-on | good | after 1–2 mins. | no symptoms |

TABLE X

| Preparation/application | Dose in mg/kg | Worm reduction compared to untreated control groups, in % | | |
|---|---|---|---|---|
| | | Haemonchus | Cooperia | Oesophagostomum |
| 10% by weight of Levamisole in isopropanol + 10% by weight of LPS pour-on | 3 | 99 | 100 | 100 |
| | 6 | 100 | 100 | 98 |

The literature gives the following values for the peroral administration of Levamisole
(H. Ciordia and Baird, Am. J. Vet. Res. Vol 30, pages 1,145–1,148 (1969)):

| dose in mg/kg | Worm reduction compared to untreated control groups, in % | | |
|---|---|---|---|
| | Haemonchus | Cooperia | Oesophagostomum |
| 8 | 100 | 100 | 97 |
| 5.4 | 100 | 100 | 99 |

EXAMPLE F

Gastro-intestinal worm test in neats/controlled test against larval stages

Neats experimentally infected with Haemonchus, Cooperia and Oesophagostomum are treated by pouring the solution of active compound onto their backs or by subcutaneous injection.

The time at which the treatment was carried out was so chosen that the larvae were in the 4th stage of development.

The activity of the preparations is determined by dissecting the animal, counting the worms remaining, comparing the result to that obtained with untreated control animals, and calculating the percentage action.

The results of this study are indicated in Table XI below:

TABLE XI

| Preparation/application | dose in mg/kg | Worm reduction compared to untreated control group, in % | | |
|---|---|---|---|---|
| | | Haemonchus | Cooperia | Oesophagostomum |
| 10% by weight of Levamisole in isopropanol + 10% by weight of LPS pour-on | 6 | 93 | 100 | 94 |
| 10% strength aqueous Levamisole solution, subcutaneous | 6.5 | 99 | 99 | 81 |
| For comparison:* Levamisole oral | 8 | 53 | 100 | |

*Literature: Lyons et al., Am. J. Vet. Res. Vol 33, No. 1, 65–71 (1972)

EXAMPLE G

Gastro-intestinal worm test in neats/excretion of eggs

Neats infected experimentally or naturally with various species of gastro-intestinal worms (Cooperia, Ostertagia, Trichostrongylus, Bunostomum and Oesophagostomum) were treated at the end of the prepatency period of the parasites by pouring a solution of the active compound onto their backs.

The activity is determined by quantitatively counting the worm eggs excreted with the faeces before and after the treatment.

A decrease in egg excretion after the treatment indicates that the worms have been expelled or are so severely damaged that they cannot produce any more eggs.

The results of this study are indicated in Table XII below:

TABLE XII

| Preparation/application | Dose in mg/kg | Reduction in egg excretion in % |
|---|---|---|
| Tetramisole in isopropanol, pour-on | 10 | 87 |
| | 5 | 39 |
| Tetramisole in isopropanol + LPS, pour-on | 10 | 99 |
| | 5 | 76 |
| Levamisole in isopropanol + LPS, pour-on | 10 | 95 |
| | 5 | 91 |
| For comparison:* Levamisole oral | 8 | 99 |

*Literature: Lyons et al., Am. J. Vet. Res. Vol 33, No. 1, 65–71 (1972)

EXAMPLE H

Gastro-intestinal worm test in sheep

Sheep experimentally infected with Haemonchus or Cooperia were treated at the end of the prepatency period of the parasites by pouring the active substance solution onto their backs.

The activity is determined by quantitatively counting the worm eggs excreted with the faeces before and after the treatment.

A decrease in egg excretion after the treatment indicates that the worms have been expelled or are so severely damaged that they cannot produce any more eggs.

The results of this study are indicated in Table XIII below:

TABLE XIII

| Preparation/application | Dose in mg/kg | Reduction in excretion of eggs, in % | |
|---|---|---|---|
| | | Haemonchus | Cooperia |
| 10% by weight of Levamisole in isopropanol | 25 | 98 | — |

TABLE XIII-continued

| Preparation/application | Dose in mg/kg | Reduction in excretion of eggs, in % | |
|---|---|---|---|
| | | Haemonchus | Cooperia |
| + 10% by weight of LPS pour-on | 10 | 84 | 100 |
| | 5 | 97 | 99 |
| | 2.5 | 51 | 67 |

EXAMPLE I

Determination of level in the blood

The resorption of the anthelmintic agent can be estimated, with less trouble than with the method described above, by determining the level of the agent in the blood after administration. The blood levels in neats after treatment with 20 mg of Levamisole/kg were determined.

The pour-on method (Levamisole in various solvents) was compared with peroral administration (2 percent strength aqueous Levamisole solution) and subcutaneous administration (10 percent Levamisole in 0.9 percent strength aqueous NaCl solution).

Method

The active compound was isolated from the blood by the method of Holbrock and Scales (Analyt. Biochem. 18, 46–53 (1957)). The quantitative determination was carried out spectrophotometrically by measuring the extinction at a wave length of 215 nm.

Using the pour-on method it is possible to achieve blood levels as high as, or higher than, those after peroral or subcutaneous administration. Only two hours after treatment does subcutaneous administration give higher blood levels than the pour-on method. High blood levels, that is to say good resorption of the active compound, are the prerequisite for successful anthelmintic use of the active compound.

The following tables show the blood level of the active compound in μg/ml at various times after administration in the stated manner of 20 mg/kg body weight.

| Composition of the pour-on formulation | Number of animals | Number of blood level determinations | Blood level in μg/ml after | | |
|---|---|---|---|---|---|
| | | | 2 hours | 4 hours | 6 hours |
| 10 g of Levamisole + 10 g of LPS made up to 100 ml with isopropanol | 3 | 27–29 | 0.79 | 0.70 | 0.59 |
| 10 g of Levamisole + * 10 g of LPS made up to 100 ml with chloroform | 3 | 9 | 0.97 | 0.86 | 0.71 |
| 10% of Levamisole + 20% of polyoxyethylated castor oil + isopropyl myristate | 2 | 6 | 0.64 | 0.72 | 0.76 |
| 10% of Levamisole + 7.5% of sorbitane monooleate + 10% of $CHCL_3$ + isopropyl myristate | 3 | 9 | 1.26 | 1.42 | 1.17 |
| 10% of Levamisole + 7.5% of lecithin + 10% of $CHCl_3$ + isopropyl myristate | 3 | 9 | 1.00 | 1.20 | 0.96 |
| 10% of Levamisole + 10% of LPS + methylene chloride | 1 | 3 | 1.00 | 1.89 | 0.85 |
| 10% of Levamisole + 10% sorbitane monooleate + decahydronaphthalene | 1 | 3 | 0.67 | 1.16 | 0.94 |
| 10% of Levamisole + 15% of sorbitane monooleate + phthalic acid butyl ester | 3 | 8–9 | 0.99 | 1.02 | 0.88 |
| 10% of Levamisole + 25% of dimethyl sulphoxide + isopropanol | 2 | 5–6 | 0.94 | 0.29 | 0.25 |
| 10% of Levamisole in methyl ethyl ketone | 3 | 8–9 | 0.77 | 0.58 | 0.43 |
| 10% of Levamisole + 20% of methyl ethyl ketone + isopropyl myristate | 3 | 8–9 | 2.07 | 2.13 | 1.65 |
| 10% of Levamisole + 20% of dimethyl sulphoxide + 7.5% of polyoxyethylated castor oil + 8.54% of methyl ethyl ketone + isopropyl myristate | 3 | 9 | 0.65 | 0.65 | 0.49 |
| 10% of Levamisole + 7.5% * of lecithin + 20% of $CH_2Cl_2$ + isopropyl myristate | 3 | 9 | 1.79 | 2.44 | 1.91 |
| 10% of Levamisole + 7.5% of polyoxyethylated castor oil + 20% of $CH_2Cl_2$ + isopropyl myristate | 3 | 9 | 2.11 | 1.91 | 1.50 |
| 10% of Levamisole + 7.5% of polyoxyethylated * | | | | | |

| Composition of the pour-on formulation | Number of animals | Number of blood level determinations | Blood level in μg/ml after | | |
|---|---|---|---|---|---|
| | | | 2 hours | 4 hours | 6 hours |
| castor oil + 10% of CHCl₃ + isopropyl myristate | 3 | 9 | 1.45 | 2.85 | 2.60 |
| 10% of Levamisole + 7.5% of polyoxyethylated * castor oil + 20% of CH₂Cl₂ + 10% of isopropanol + isopropyl myristate | 3 | 9 | 1.17 | 1.80 | 1.83 |
| 10% of Levamisole + 7.5% of polyoxyethylated * castor oil + 30% of CH₂Cl₂ + isopropyl myristate | 3 | 8–9 | 1.48 | 2.10 | 1.81 |
| 5% of Levamisole + 7.5% * of polyoxyethylated castor oil + 20% of CH₂Cl₂ + 10% of isopropanol + isopropyl myristate | 3 | 8–9 | 2.32 | 2.22 | 1.58 |
| 5% of Levamisole + 7.5% of polyoxyethylated castor oil + 30% of * CH₂Cl₂ + isopropyl myristate | 3 | 8–9 | 2.73 | 2.35 | 1.61 |
| Composition for peroral administration 2% strength aqueous Levamisole solution | 3 | 9 | 1.80 | 1.36 | 1.01 |

*While good blood levels are achieved, contraindications have been observed due to the chlorinated hydrocarbons
In each of the above formulations, the ingredient without a percentage or amount is present in the amount necessary to make up 100% by weight.

What is claimed:

1. A pour-on veterinary composition useful for the treatment of helminthic infestations in animals which comprises from 1 to 20 percent by weight of tetramisole, levamisole or a nontoxic acid addition salt thereof in combination with ethanol or isopropanol as diluent suitable for pour-on therapy.

2. A composition according to claim 1 wherein the tetramisole, levamisole, or nontoxic acid addition salt thereof, is present in the amount of 5 to 15 percent by weight.

3. A composition according to claim 1 which comprises 1 to 20 percent by weight tetramisole or levamisole, 10 to 94 percent by weight of ethanol or isopropanol, and 5 to 89 percent by weight of a liquid paraffin.

4. A composition according to claim 3 which comprises 5 to 15 percent by weight of tetramisole or levamisole, 60 to 90 percent by weight of said ethanol or isopropanol and 5 to 30 percent by weight of a liquid paraffin which is a light and purified spindle oil distillate.

5. A pour-on veterinary composition useful for the treatment of helminthic infestation in animals which comprises 1 to 20 percent by weight of tetramisole or levamisole, 10 to 94 percent by weight of a mono- or di-lower alkyl ester of phthalic acid and 5 to 50 percent by weight of a nonionic surface active agent.

6. A composition according to claim 5 wherein the tetramisole or levamisole is present in the amount of 5 to 15 percent by weight and the ester is present in the amount of 60 to 90 percent by weight.

7. A composition according to claim 5 wherein the ester is the dibutyl ester of phthalic acid.

8. A composition according to claim 7 wherein the surface active agent is an ester of sorbitan and a fatty acid with polyoxyethylene or an ester of sorbitan and a fatty acid.

9. A composition according to claim 1 which comprises 10 percent by weight levamisole, 80 percent by weight isopropanol and 10 percent by weight light and purified spindle oil distillate.

10. A composition according to claim 1 which comprises 10 percent by weight levamisole, 75 percent by weight phthalic acid dibutyl ester and 15 percent sorbitan mono-oleate.

11. A method for treating helminthic infestations in animals which comprises pouring onto the external skin of the animal to be treated an effective amount of a composition according to claim 1.

12. A method for treating helminthic infestations in animals which comprises pouring onto the external skin of the animal to be treated an effective amount of a composition according to claim 2.

13. A method for treating helminthic infestations in animals which comprises pouring onto the external skin of the animal to be treated an effective amount of a composition according to claim 3.

14. A method for treating helminthic infestations in animals which comprises pouring onto the external skin of the animal to be treated an effective amount of a composition according to claim 4.

15. A method for treating helminthic infestations in animals which comprises pouring onto the external skin of the animal to be treated an effective amount of a composition according to claim 5.

16. A method for treating helminthic infestations in animals which comprises pouring onto the external skin of the animal to be treated an effective amount of a composition according to claim 6.

17. A method for treating helminthic infestations in animals which comprises pouring onto the external skin of the animal to be treated an effective amount of a composition according to claim 7.

18. A method for treating helminthic infestations in animals which comprises pouring onto the external skin of the animal to be treated an effective amount of a composition according to claim 8.

19. A method for treating helminthic infestations in animals which comprises pouring onto the external skin of the animal to be treated an effective amount of a composition according to claim 9.

20. A method for treating helminthic infestations in animals which comprises pouring onto the external skin of the animal to be treated an effective amount of a composition according to claim 10.

21. The method of claim 11 wherein the effective amount is from about 1 mg/kg to 20 mg/kg of body weight of the animal.

22. The method of claim 11 wherein the animal is a sheep and the effective amount is from about 5 mg/kg to 10 mg/kg of body weight of said animal.

23. The method of claim 11 wherein the animal is a neat and the effective amount is from about 5 mg/kg to 15 mg/kg of body weight of said animal.

24. The method of claim 11 wherein the animal is a dog and the effective amount is from about 8 mg/kg to 12 mg/kg of body weight of said animal.

25. The method of claim 11 wherein the animal is a pig and the effective amount is from about 10 mg/kg to 20 mg/kg of body weight of said animal.

26. A composition according to claim 1 wherein tetramisole or levamisole is present in the amount of 1 to 20 percent by weight.

27. A composition according to claim 1 wherein tetramisole or levamisole is present in the amount of 5 to 15 percent by weight.

28. A composition according to claim 1 wherein tetramisole or levamisole is present in the amount of 10 percent by weight.

29. A composition according to claim 1 which comprises from 1 to 20 percent by weight of tetramisole or levamisole and wherein the diluent is isopropanol.

30. A composition according to claim 1 which comprises from 5 to 15 percent by weight of tetramisole or levamisole and wherein the diluent is isopropanol.

31. A composition according to claim 1 which additionally contains 5 to 50 percent by weight of a suitable surface active agent.

32. A composition according to claim 3 wherein ethanol is present in the amount of 10 to 94 percent by weight.

33. A composition according to claim 3 wherein isopropanol is present in the amount of 10 to 94 percent by weight.

34. A composition according to claim 4 wherein ethanol is present in the amount of 60 to 90 percent by weight.

35. A composition according to claim 4 wherein isopropanol is present in the amount of 60 to 90 percent by weight.

36. A composition according to claim 1 wherein the nontoxic acid addition salt is the hydrochloride salt.

37. A method for treating helminthic infestations in animals which comprises pouring onto the external skin of the animal to be treated an effective amount of a composition according to claim 26.

38. A method for treating helminthic infestations in animals which comprises pouring onto the external skin of the animal to be treated an effective amount of a composition according to claim 27.

39. A method for treating helminthic infestations in animals which comprises pouring onto the external skin of the animal to be treated an effective amount of a composition according to claim 28.

40. A method for treating helminthic infestations in animals which comprises pouring onto the external skin of the animal to be treated an effective amount of a composition according to claim 29.

41. A method for treating helminthic infestations in animals which comprises pouring onto the external skin of the animal to be treated an effective amount of a composition according to claim 30.

42. A method for treating helminthic infestations in animals which comprises pouring onto the external skin of the animal to be treated an effective amount of a composition according to claim 31.

43. A method for treating helminthic infestations in animals which comprises pouring onto the external skin of the animal to be treated an effective amount of a composition according to claim 32.

44. A method for treating helminthic infestations in animals which comprises pouring onto the external skin of the animal to be treated an effective amount of a composition according to claim 33.

45. A method for treating helminthic infestations in animals which comprises pouring onto the external skin of the animal to be treated an effective amount of a composition according to claim 34.

46. A method for treating helminthic infestations in animals which comprises pouring onto the external skin of the animal to be treated an effective amount of a composition according to claim 35.

47. A method for treating helminthic infestations in animals which comprises pouring onto the external skin of the animal to be treated an effective amount of a composition according to claim 36.

* * * * *

UNITED STATES PATENT AND TRADEMARK OFFICE
CERTIFICATE OF CORRECTION

PATENT NO. : 3,980,791
DATED : September 14, 1976
INVENTOR(S) : HANS PETER SCHULZ ET AL It is certified that error appears in the above-identified patent and that said Letters Patent are hereby corrected as shown below:

In the title page of the patent under

"References Cited"
UNITED STATES PATENTS insert

| | | | |
|---|---|---|---|
| -- 3,463,786 | 8/1969 | Bullock | 260/306.7 |
| 3,364,112 | 1/1968 | Raeymaekers et al | 167/55 |
| 3,274,209 | 9/1966 | Raeymaekers et al | 260/306.7 |
| 3,177,118 | 4/1965 | Baetz | 167/65 |
| 3,792,166 | 2/1974 | Spicer et al | 424/270 |
| 3,670,085 | 6/1972 | Pryor et al | 424/270 |
| 3,679,696 | 7/1972 | Bullock | 260/306 |
| 3,642,809 | 2/1972 | Bullock | 260/306.7 |
| 3,592,936 | 7/1971 | Marcus et al | 424/337 |
| 3,551,554 | 12/1970 | Herschler | 424/7 --. |

Signed and Sealed this

Twenty-second Day of March 1977

[SEAL]

Attest:

RUTH C. MASON
*Attesting Officer*

C. MARSHALL DANN
*Commissioner of Patents and Trademarks*

UNITED STATES PATENT OFFICE
CERTIFICATE OF CORRECTION

Patent No. 3,980,791　　　　Dated September 14, 1976

Inventor(s) Hans Peter Schulz et al.

It is certified that error appears in the above-identified patent and that said Letters Patent are hereby corrected as shown below:

Column 13, line 35, after "as" insert -- a --.

Signed and Sealed this

Eighteenth Day of October 1977

[SEAL]

Attest:

RUTH C. MASON  
Attesting Officer

LUTRELLE F. PARKER  
Acting Commissioner of Patents and Trademarks

Notice of Adverse Decision in Interference

In Interference No. 99,912, involving Patent No. 3,980,791, H. P. Schulz and H. Voege, TETRAMISOLE AND LEVAMISOLE POUR-ON ANTHELMINTIC COMPOSITIONS AND METHOD OF USE, final judgment adverse to the patentees was rendered Feb. 13, 1981, as to claims 1-3, 11-13, 21-33, 36-44 and 47.

[*Official Gazette August 25, 1981.*]

Disclaimer 3,980,791.—*Hans Peter Schulz*, Wuppertal; and *Herbert Voege*, Opladen-Bruchhausen, Germany. TETRAMISOLE AND LEVAMISOLE POUR-ON ANTHELMINTIC COMPOSITIONS AND METHODS OF USE. Patent dated Sept. 14, 1976. Disclaimer filed Apr. 30, 1981, by the assignee, *Bayer Aktiengesellschaft*.

Hereby enters this disclaimer to claims 1-3, 11-13, 21-33, 36-44, and 47 of said patent.

[*Official Gazette August 10, 1982.*]